(12) United States Patent
Mikhail

(10) Patent No.: US 6,228,092 B1
(45) Date of Patent: May 8, 2001

(54) SYSTEM FOR PERFORMING HIP PROSTHESIS SURGERY

(76) Inventor: W. E. Michael Mikhail, 4203 Shamley Green, Toledo, OH (US) 43623

( * ) Notice: Subject to any disclaimer, the term of this patent is extended or adjusted under 35 U.S.C. 154(b) by 0 days.

(21) Appl. No.: 09/363,448

(22) Filed: Jul. 29, 1999

(51) Int. Cl.$^7$ .................................................. A61B 17/58
(52) U.S. Cl. ............................................. 606/105; 606/86
(58) Field of Search ............................... 606/105, 80–90; 623/16, 20, 23

(56) References Cited

U.S. PATENT DOCUMENTS

| | | | |
|---|---|---|---|
| 4,274,408 | 6/1981 | Nimrod | 604/16 |
| 4,337,773 | 7/1982 | Raftopoulos et al. | 606/62 |
| 4,338,925 | 7/1982 | Miller | 606/94 |
| 4,341,206 | 7/1982 | Perrett et al. | 606/80 |
| 4,399,814 | 8/1983 | Pratt, Jr. et al. | 128/92 |
| 4,623,353 | 11/1986 | Buechel et al. | 623/23 |
| 4,678,471 | 7/1987 | Noble et al. | 606/80 |
| 4,686,972 | 8/1987 | Kurland | 606/96 |
| 4,706,659 | 11/1987 | Mathews et al. | 606/80 |
| 4,751,922 | 6/1988 | DiPietropolo | 606/80 |
| 4,815,454 | 3/1989 | Dozier, Jr. | 128/92 |
| 4,846,161 | 7/1989 | Roger | 606/99 |
| 4,860,735 | 8/1989 | Davey et al. | 606/80 |
| 4,865,608 | 9/1989 | Brooker, Jr. | 623/23 |
| 4,873,969 | 10/1989 | Huebsch | 606/80 |
| 4,881,536 | 11/1989 | Nobel et al. | 606/80 |
| 4,896,662 | 1/1990 | Noble | 606/94 |
| 4,904,262 | * 2/1990 | Bensmann | 623/18 |
| 4,919,153 | 4/1990 | Chin | 606/93 |
| 4,919,673 | 4/1990 | Willert et al. | 623/23 |
| 4,919,679 | 4/1990 | Averill et al. | 623/23 |
| 4,963,155 | 10/1990 | Lazzeri et al. | 623/23 |
| 4,986,826 | 1/1991 | Roger | 606/82 |
| 4,994,065 | 2/1991 | Gibbs et al. | 606/92 |
| 4,994,085 | 2/1991 | Sawai et al. | 623/23 |
| 5,015,817 | 5/1991 | Kranz | 623/23 |

(List continued on next page.)

FOREIGN PATENT DOCUMENTS

| | | |
|---|---|---|
| 3108491 | 11/1981 | (DE) . |
| 2615097 | 5/1987 | (FR) . |
| 0 315 283 | 11/1988 | (GB) . |
| 92/03993 | 3/1992 | (WO) . |

OTHER PUBLICATIONS

International Search Report for PCT/US00/19114 which corresponds to this U.S. patent application.

Kenneth J. Hock, M.D., "Economy is the Mother of a Cement Removal Technique", *Orthopedics Today*, pp. 18 & 19, Sep. 1989.

Waldes Truarc Retaining Rings, Jan. 1981, p. 5 (Selector Guide).

John N. Insall, M.D., et al., "Principles and Techniques of Knee Replacement", published in 1983 by New York Society for the Relief of the Ruptured and Crippled, pp 20–21.

John Insall, M.D. and Albert H. Burstein, Ph.D., "Insall/Burstein™ Total Knee System" Pamphlet.

W.E. Michael Mikhail, M.D. and Lars Weidenhielm, M.D., "The CPT Hip Prosthesis" Pamphlet (1994).

Osteonics Restoration Cemented Hip System for Revision Surgery, 4 pages.

*Primary Examiner*—Henry J. Recla
*Assistant Examiner*—Lien Ngo
(74) *Attorney, Agent, or Firm*—Emch, Schaffer, Schaub & Porcello, Co., L.P.A.

(57) ABSTRACT

A cannulated tamp for preparing a cavity in a femur to receive a prosthesis has a thin sidewall with perforations and openings at the proximal and distal ends. During the process of tamping bone graft material, it is positioned over a guide wire which extends through the openings at the proximal and distal ends. After completion of the tamping, the guide wire is removed and a perforated tubing attached to a vacuum pump is inserted through the openings at the proximal and distal ends to withdraw liquids from the prepared cavity.

14 Claims, 5 Drawing Sheets

U.S. PATENT DOCUMENTS

| | | | |
|---|---|---|---|
| 5,021,063 | 6/1991 | Tager | 623/23 |
| 5,047,035 | 9/1991 | Mikhail et al. | 606/93 |
| 5,047,061 | 9/1991 | Brown | 623/23 |
| 5,061,287 | 10/1991 | Feiler | 623/16 |
| 5,078,746 | 1/1992 | Garner | 623/16 |
| 5,085,548 | 2/1992 | Moyles | 411/522 |
| 5,108,405 | 4/1992 | Mikhail et al. | 606/96 |
| 5,116,377 | 5/1992 | Skripitz | 623/23 |
| 5,192,282 | 3/1993 | Draeuert | 606/65 |
| 5,192,283 | 3/1993 | Ling et al. | 606/93 |
| 5,197,841 | 3/1993 | Tanaka | 411/353 |
| 5,201,769 | 4/1993 | Schutzer | 623/23 |
| 5,314,489 | 5/1994 | Hoffman et al. | 623/22 |
| 5,330,536 * | 7/1994 | Tager et al. | 623/23 |
| 5,366,441 | 11/1994 | Crawford et al. | 604/53 |
| 5,443,469 | 8/1995 | Smith | 606/86 |
| 5,470,336 | 11/1995 | Ling et al. | 606/95 |
| 5,480,452 | 1/1996 | Hofmann et al. | 623/23 |
| 5,507,830 | 4/1996 | De Mane et al. | 623/23 |
| 5,514,135 | 5/1996 | Earle | 606/93 |
| 5,683,395 * | 11/1997 | Mikhail | 606/86 |
| 5,693,099 * | 12/1997 | Harle | 623/16 |
| 5,707,049 | 1/1998 | Schmidt . | |
| 5,718,707 | 2/1998 | Mikhail | 606/94 |
| 5,800,437 | 9/1998 | Gustilo et al. | 606/86 |
| 5,814,049 | 9/1998 | Pratt et al. . | |
| 5,925,051 | 7/1999 | Mikhail | 606/94 |

* cited by examiner

SYSTEM FOR PERFORMING HIP PROSTHESIS SURGERY

BACKGROUND ART

U.S. Pat. Nos. 5,192,283 and 5,470,336, for which I am co-inventor, are directed to a method and apparatus for performing hip prosthesis revision surgery which includes preparation of the enlarged cavity left after removal of the original prosthesis. A tamp having a longitudinal passageway extending longitudinally through the stem portion thereof and a guide wire positioned in the cavity function to compact bone graft material in the enlarged cavity and form a contoured cavity for receiving the new hip prosthesis. The tamp disclosed in such patents provides good compaction of the bone graft material contacted by the tapered stem from the distal end to an area somewhat spaced from the proximal end. However, the tamp disclosed in such prior art patents has no ability to provide compaction for bone graft material in the vicinity of the proximal end of the femur. My U.S. Pat. No. 5,683,395 discloses and claims a cannulated tamp having a flange extending outwardly from the proximal end of the tamp. One embodiment of my U.S. Pat. No. 5,683,395 discloses a tamp which has a stem and a network of connector passageways which may be utilized to drain blood and other liquids from the cavity being prepared.

DISCLOSURE OF THE INVENTION

The present invention is directed to a cannulated tamp and to a method for using, which tamp is formed as a hollow member with walls having a thickness of ½ to 3 millimeters (mm). It is provided with perforations throughout, which perforations are 2 to 5 mm in diameter. The tamp has a smooth outer surface which is preferably polished and tapers from a relatively large size at its proximal end to a smaller size at its distal end. If desired, it may be triple tapered. Preferably, it is shaped similar to the shape of the stem of the femoral hip prosthesis to be implanted in the prepared cavity; however, where it is to be used in preparing a cavity to receive a femoral stem prosthesis of a type utilizing bone cement, the tamp will be oversized (i.e. larger than the intended femoral stem prosthesis) at least 2 mm circumferentially in order to allow space in the cavity for an adequate thickness of bone cement between the stem of the prosthesis and the wall of the prepared cavity. Proximally medially it should be oversized 4–6 mm and the length should be oversized 15–30 mm. The distal end of the tamp tapers to an opening through which a guide wire may extend. The proximal end of the tamp has a wall with an aperture for receiving the guide wire. The guide wire controls the positioning of the tamp during use of the tamp for compacting the bone graft material. Following compacting of the bone graft material, the proximal and distal guide wire openings may be used to receive a suction tube extending through the perforated tamp. The proximal end is also provided with a handle attachment abutment which may be engaged by a handle and, if desired, a second opening which may be utilized for inserting a second vacuum tube into the cannulated tamp.

The cannulated perforated tamp of the present invention may be formed from a wide variety of materials including cobalt chrome molybdenum, stainless steel, titanium or a compatible durable material.

BEST MODE OF CARRYING OUT INVENTION

Figure 1:
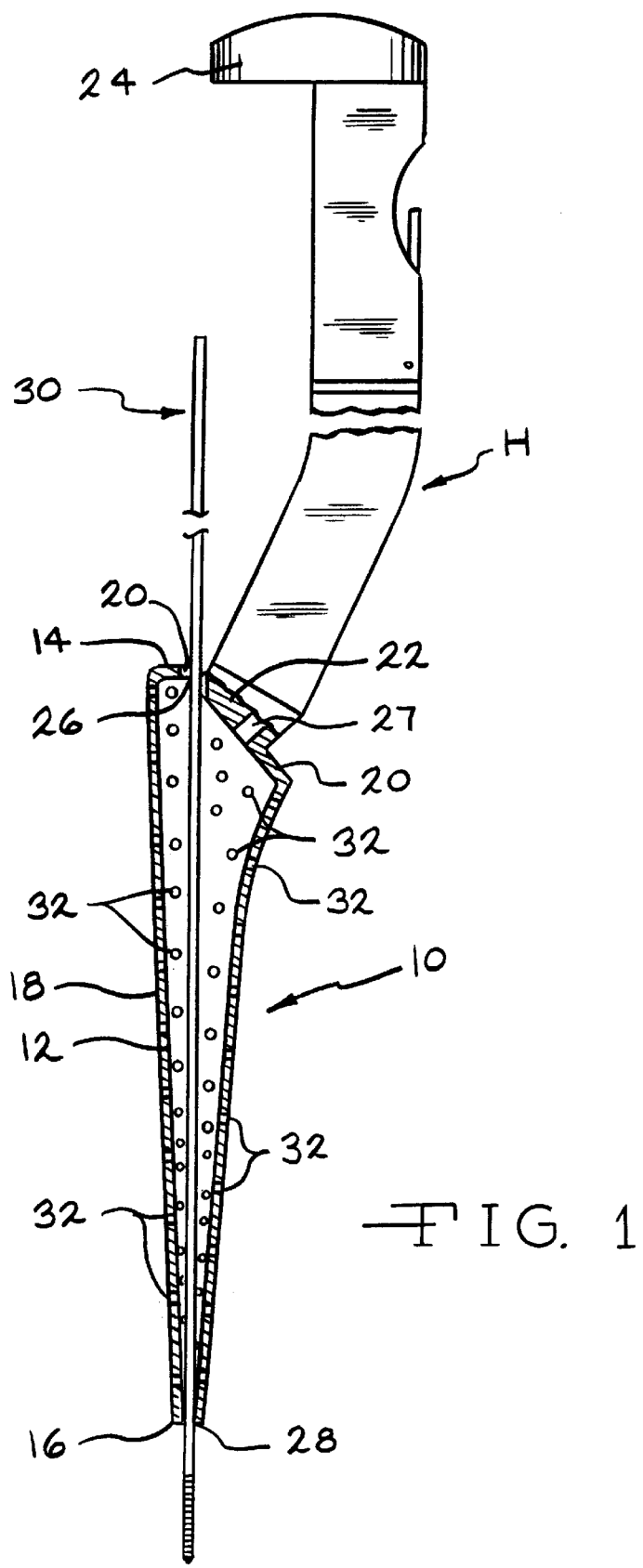
FIG. 1 is an elevational view, partly in section, showing the tamp of the present invention, along with an associated guide wire and handle.
Figure 2:
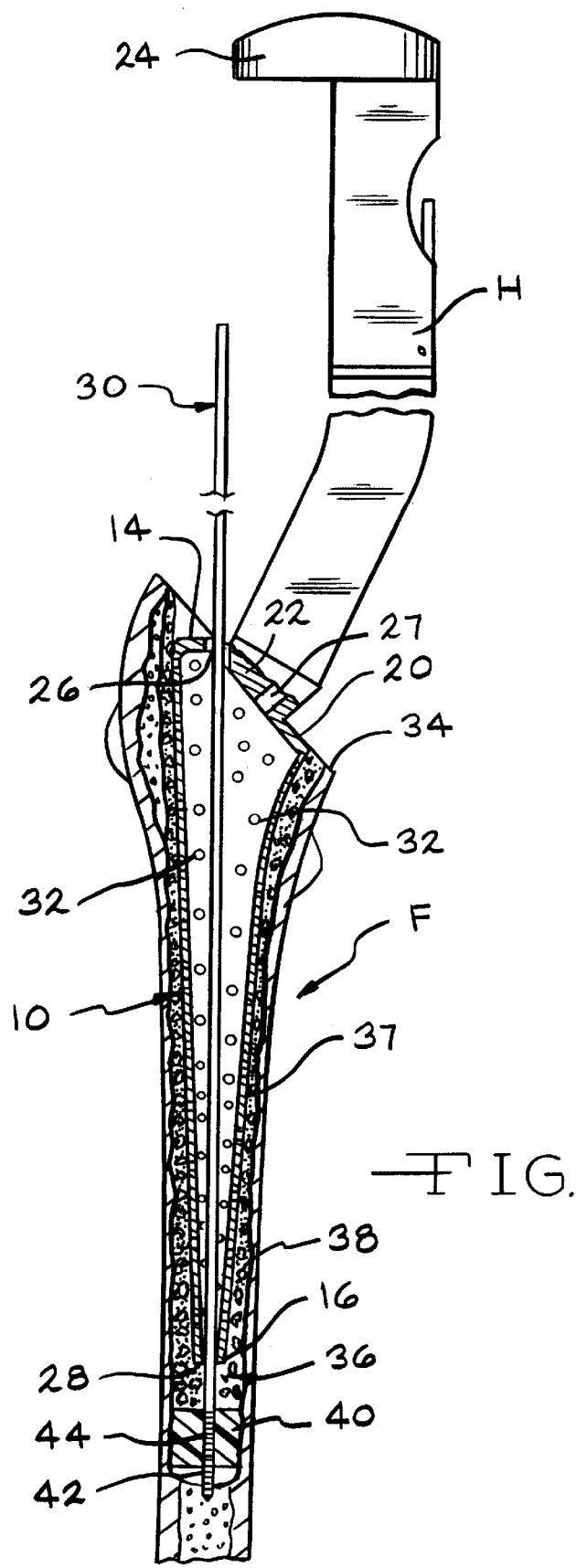
FIG. 2 is an elevational view, partly in section, showing the tamp of the present invention, compacting morsellized bone graft to define a cavity prepared to receive a femoral prosthesis utilizing the method and apparatus of the present invention.

Referring to FIGS. 1 and 2, there is shown a cannulated tamp generally designated by the numeral 10 having a stem 12 extending from an upper proximal end 14 to a lower distal end 16. The tamp 10 may be of any desired cross-sectional configuration and preferably has a cross-sectional configuration and overall shape similar to that of the stem of a femoral hip prosthesis which is to be positioned in the cavity of the femur being prepared by the tamp 10. For example, the stem 12 has an exterior surface 18, which exterior surface 18 could have a cross-sectional configuration such as that shown in U.S. Pat. No. 5,171,275 of which I am a co-inventor. In those cases in which the tamp 10 is to be utilized for preparing a cavity to receive a femoral stem prosthesis which does not utilize bone cement, the size of the stem at the exterior surface 18 will be substantially the same size as that of the stem of the prosthesis intended to be implanted in the prepared cavity. In those instances in which the tamp 10 is to be utilized in preparing a cavity for receiving a prosthesis intended to be implanted with bone cement, the stem 12 at the exterior surface 18 will be larger than the stem of the prosthesis in order to provide space to receive bone cement between the stem and surface of the prepared cavity, which bone cement should preferably have a thickness on the order of 2 to 4 mm circumferentially of the stem, except medially in the proximal area which desirably has a thickness of 4 to 6 mm. Additionally, the tamp 10 should have length longer than the stem of the prosthesis by 15 to 30 mm.

The proximal end 14 defines a wall 20 having a gripping abutment 22 to which may be engaged by a handle H for holding the tamp 10 by any conventional locking mechanism. The handle H may have an enlarged head 24 for receiving blows from a compaction hammer. The proximal wall 20 is provided with a first aperture 26 and a second aperture 27, each having a preferable size of 5 to 10 mm in diameter. The distal end 16 has an opening 28 aligned with the aperture 26. A guide wire 30 which has been inserted through the aperture 26 will extend through the opening 28. Preferably, the opening 28 at the distal end 16 is on the order of 2 to 4 mm in diameter.

The stem 12 preferably has a wall thickness of 1 to 4 mm and is provided throughout with a series of apertures 32 each having a diameter in the range of 2 to 4 mm.

FIG. 2 shows the tamp 10 positioned in a femur F having a prepared proximal end 34. The femur F has an enlarged cavity 36 in which has been positioned bone graft material 38. The bone graft material 38 is shown as having been compacted by the tamp 10 in the enlarged cavity 36 to form a prepared cavity 37. As is well known in the art, a plug or restrictor 40 is preferably positioned in the distal end of the enlarged cavity 36. The guide wire 30 may have threads 42 at its distal end threadedly engaged to a central aperture 44 of the restrictor 40. The guide wire 30 extending through the proximal aperture 26 and distal opening 28 and secured to the restrictor 40 serves to accurately control the position of the tamp 10 while compacting the bone graft material 38.

Figure 3:
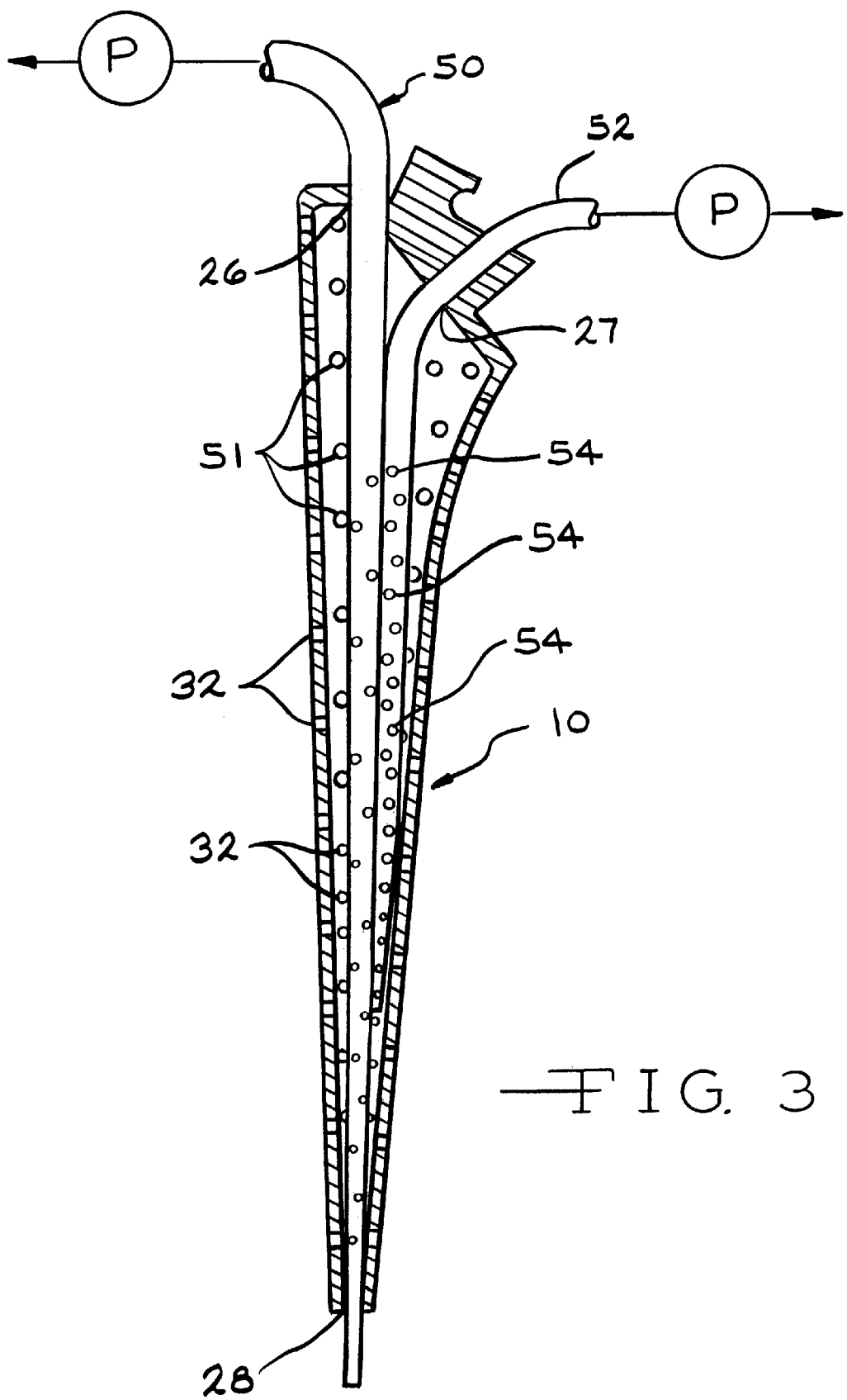
FIG. 3 is an elevational view, partly in section, showing the tamp and a pair of vacuum tubes positioned therein.
Figure 4:
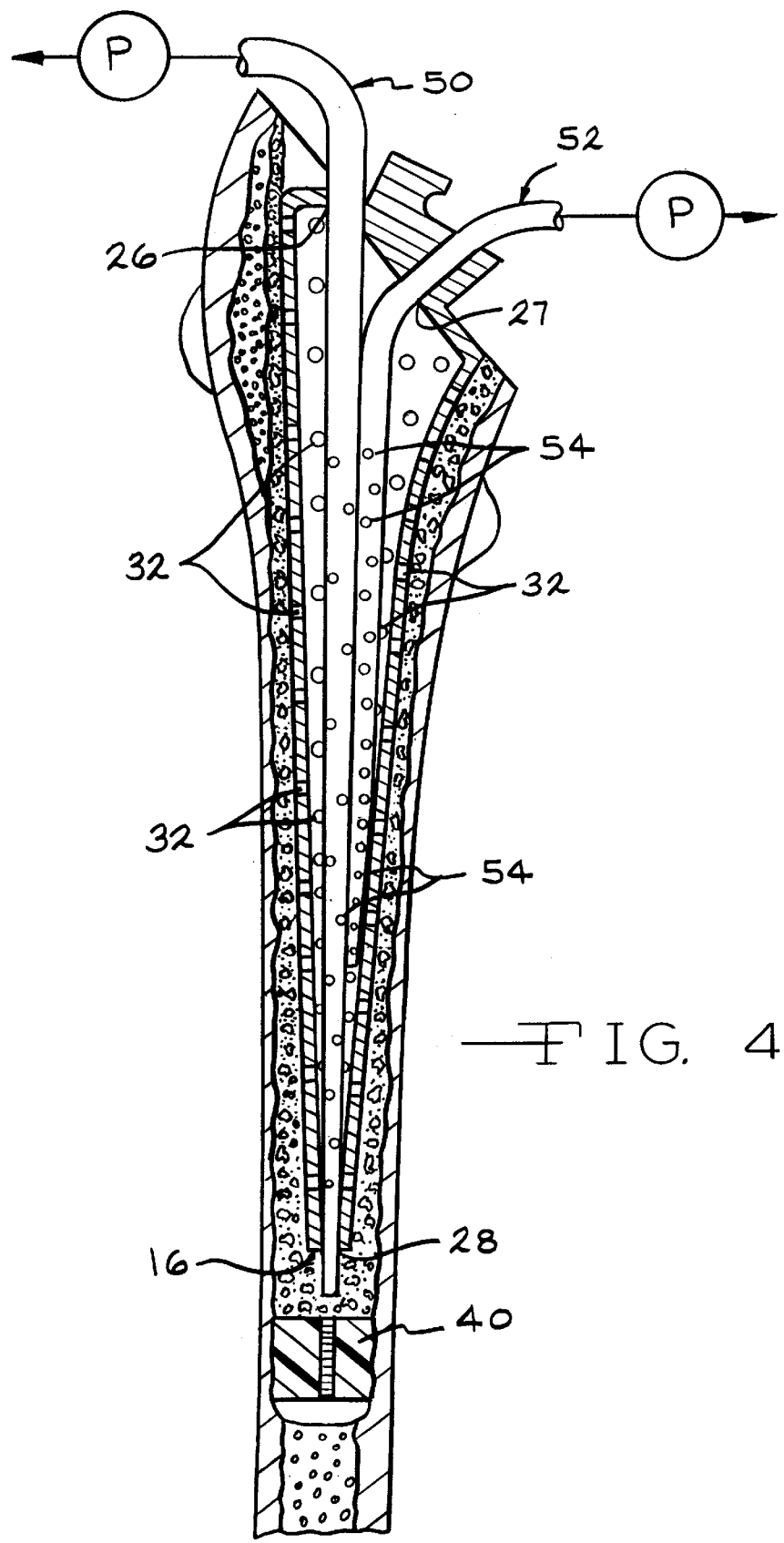
FIG. 4 is a view similar to FIG. 3, but showing the utilization of the system for removing blood and other liquids from the cavity being prepared.

Referring to FIGS. 3 and 4, there is shown positioned in the tamp 10 a first vacuum tube 50 which is connected to a vacuum pump P. If desired, a second vacuum tube 52 may also be positioned in the tamp 10. The first vacuum tube 50 has apertures 51 throughout and extends through the proximal wall aperture 26, the hollow area of the tamp and out of the opening 28 at the distal end 16 and functions to remove any blood or other liquid which may have accumulated circumferentially and in the area of the distal end 16. The second vacuum tube 52 extends through the second aperture 27 in the proximal end 26. The second vacuum tube 52 will remain within the cavity of the tamp 10 and does not extend to the distal end 16. It is provided with a series of apertures 54 throughout its length in order to remove blood or other liquids from the surrounding areas of the prepared cavity 37. As will be appreciated, the blood or other liquids will flow through the apertures 32 in the stem 12 of the hollow tamp 10 and then through the apertures 51 of the first tube 50 and the apertures 54 of the second tube 52 where they are drawn out of the cavity by the respective vacuum pumps P for disposal. As can be seen in FIG. 4, the first vacuum tube 50 extends beyond the distal end 16 of the stem 10, but does not reach the restrictor 40.

Figure 5:
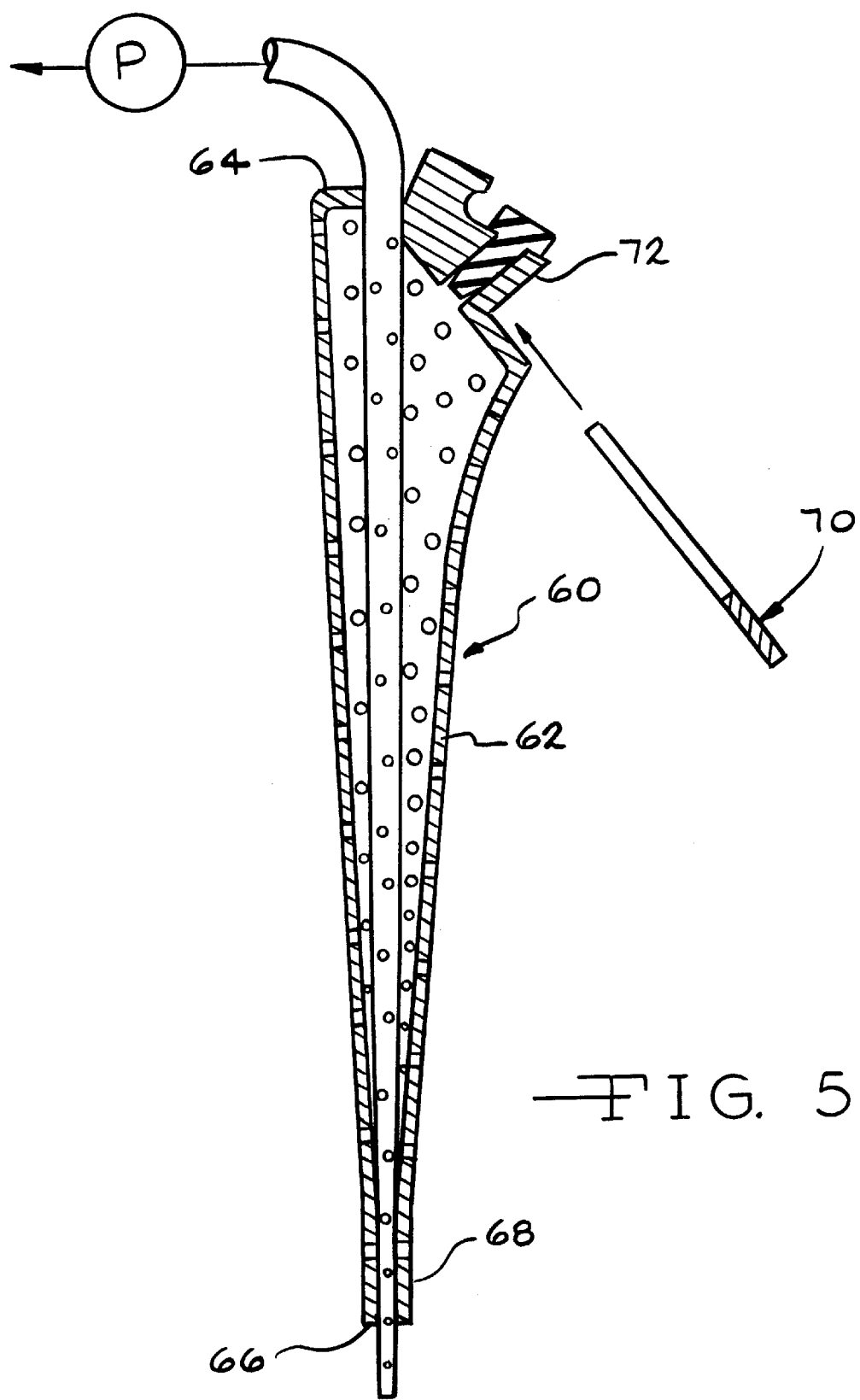
FIG. 5 is a view similar to FIGS. 1 and 3 showing another embodiment of perforated tamp.

Referring to FIG. 5, there is shown a modified embodiment of tamp 60 having a stem 62 extending from a proximal end 64 to a distal end 66. Under this embodiment, there is provided a cylindrical portion 68 adjacent the distal end 66 which extends toward the proximal end 64 a distance on the order of 15 to 20 mm.

There is also provided a removable proximal flange 70 which can be affixed to the gripping abutment 72 and utilized for compacting bone graft material at the proximal end as described in my prior U.S. Pat. No. 5,683,395, the disclosure of which is incorporated herein by reference.

The method and apparatus of the present invention is suitable for use in primary hip surgery as well as revision hip surgery. It may be used for preparing a femur to receive a collared or collarless prosthesis.

Many modifications will become readily apparent to those skilled in the art. Accordingly, the scope of the present invention should be determined only by the scope of the claims appended hereto.

I claim:

1. A method for preparing a cavity in a femur to receive the stem of a hip prosthesis comprising the steps of
    (a) providing a tamp having a stem tapering from a small cross-sectional size at its distal end to a larger cross-sectional size at its proximal end, said stem defined by a side wall encircling an open area, said side wall having a thickness in the range of 1 to 4 mm and having a plurality of apertures extending therethrough, said tamp having an open distal end and a proximal wall at its proximal end with at least one opening;
    (b) positioning said tamp over a guide wire positioned in said cavity with said guide wire extending through (i) said proximal wall opening and (ii) said open distal end;
    (c) compacting bone graft material with said tamp while using said guide wire to guide the position of said tamp during said compacting step to form a prepared cavity having a size and shape to receive said hip prosthesis stem;
    (d) withdrawing said guide wire from said tamp;
    (e) inserting a first tube in said tamp proximal wall opening; and
    (f) applying suction to cause liquid material to be removed from said prepared cavity through said side wall apertures.

2. The method according to claim 1, wherein said first tube has perforations throughout its length and said first tube is inserted through said proximal wall opening and extends outwardly beyond said open distal end.

3. The method according to claim 2, further including the steps of sealingly engaging said first tube to said tamp at said distal end.

4. The method according to claim 3, further including the step of sealingly engaging said first tube to said proximal wall.

5. The method according to claim 2, wherein said tamp proximal wall is provided with a second opening and a second tube having apertures throughout is inserted in said second proximal opening in sealing engagement with said tamp and applying suction to said second tube to withdraw fluid from said prepared cavity through said second tube apertures.

6. A tamp for compacting bone graft material in an enlarged cavity of a femur to form a prepared cavity suitable for receiving the stem of a hip prosthesis comprising
    (a) a stem extending from a proximal end to a distal end, said stem tapering from a larger cross-sectional size in the area of said proximal end to a smaller cross-sectional size in the area of said distal end, said stem being defined by one or more walls, each having a thickness in the range of 1 to 4 mm and having an inner surface and an outer surface and apertures extending therethrough from said inner surface to said outer surface, said inner wall defining (i) an open area within said stem and (ii) an opening at said distal end; and
    (b) a proximal wall joining opposing areas of said stem proximal end, said proximal wall having an aperture aligned with said distal end opening; and in combination with a first vacuum tube extending through said proximal wall aperture.

7. A tamp according to claim 6, wherein said apertures are positioned substantially throughout said stem and have a size in the range of 2 to 4 mm.

8. A tamp according to claim 6, wherein said proximal wall aperture has a size in the range of 5 to 10 mm.

9. A tamp according to claim 6, wherein said distal end opening is in the range of 2 to 4 mm.

10. A tamp according to claim 9, wherein said stem has a cylindrical portion extending from said distal end a distance not to exceed about 20 mm.

11. A tamp according to claim 6, in combination with a first vacuum tube sealingly engaged in said proximal wall aperture, said vacuum tube tapering from a larger cross-sectional size at said proximal wall aperture end to a smaller cross-section size and having (i) a distal end projecting outwardly from said stem distal end and (ii) a portion adjacent said tube distal end sealingly engaged to said stem inner surface in the area of said stem distal end.

12. The combination according to claim 11, wherein said first vacuum tube has apertures in the area between (i) said tamp proximal wall aperture and (ii) said stem distal end.

13. The combination according to claim 6, wherein said tamp has a second aperture in said proximal wall and further including a second vacuum tube extending through said second aperture and into said stem open area, said second vacuum tube having a plurality of apertures in the portion extending into said stem open area.

14. A tamp according to claim 6, further including a flange extending outwardly from said stem in the area of said proximal wall.

* * * * *